(12) United States Patent
Lin et al.

(10) Patent No.: US 7,524,505 B2
(45) Date of Patent: Apr. 28, 2009

(54) COMPOSITIONS AND METHODS FOR DUAL THERAPIES OF HAIR GRAYING AND BALDING IN FOLLICULAR DELIVERY SYSTEMS

(75) Inventors: Chai-Ching Shirley Lin, I-Lan (TW); Tsun-Yung Kuo, I-Lan (TW); Yun-Jeng Lin, Taipei (TW)

(73) Assignee: Schweitzer Biotech Company Ltd., Taipei (TW)

( * ) Notice: Subject to any disclaimer, the term of this patent is extended or adjusted under 35 U.S.C. 154(b) by 1 day.

(21) Appl. No.: 11/557,960

(22) Filed: Nov. 8, 2006

(65) Prior Publication Data

US 2007/0231265 A1 Oct. 4, 2007

Related U.S. Application Data

(60) Provisional application No. 60/735,925, filed on Nov. 10, 2005.

(51) Int. Cl.
| | |
|---|---|
| *A61K 38/17* | (2006.01) |
| *A61K 38/18* | (2006.01) |
| *A61K 38/30* | (2006.01) |
| *C07H 21/04* | (2006.01) |
| *C07K 14/47* | (2006.01) |
| *C07K 14/475* | (2006.01) |
| *C07K 14/65* | (2006.01) |

(52) U.S. Cl. ........................ 424/198.1; 514/2; 514/12; 530/399; 536/23.5

(58) Field of Classification Search ...................... None
See application file for complete search history.

(56) References Cited

U.S. PATENT DOCUMENTS

2005/0080250 A1  4/2005 Zsebo et al.

OTHER PUBLICATIONS

Randall et al. Stem cell factor/c-Kit signalling in normal and androgenetic alopecia hair follicles. J Endocrinol 197: 11-23, 2008.*
Tang et al. The expression of insulin-like growth factor 1 in follicular dermal papillae correlates with therapeutic efficacy of finasteride in androgenetic alopecia. J Am Acad Dermatol 49(2): 229-332, 2003.*
Broudy, V. C. (1997) Stem cell factor and hematopoiesis. Blood 90:1345-1364.
Botchkareva, N. V., M. Khlgatian, B. J. Longley, V. A. Botchkarev, B. A. Gilchrest, 2001. SCF/c-KIT signaling is required for cyclic regeneration of the hair pigmentation unit. FASEB J. 15(3):645-658.
Botchkareva, N. V., V. A. Botchkarev, B. A. Gilchrest. 2003. Fate of melanocytes during development of the hair follicle pigmentary unit. J. Investig. Dermatol. Symp. Proc. 8(1):76-79.
Frankel, S. K., B. M. Moats-Staats, C. D. Cool, M. W. Wynes, A. D. Stiles, D. W. Riches. 2005. Human insulin-like growth factor-IA expression on transgenic mice promotes adenomatous hyperplasia but not pulmonary fibrosis. Am. J. Physiol. Lung CII Mol. Physiol. 288(5):L805-812.
Guyonneau, L., F. Murisier, A. Rossier, A. Moulin, F. Beermann. 2004. Melanocytes and pigmentation are affected in dopachrome tautomerase knockout mice. Mol. Cell Biol. 24:3396-3403.
Hemesath, T. J., E. R. Price, C. Takemoto, T. Badalian, D. E. Fisher. 1998. MAP kinase links the transcription factor microphthalmia to c-kit signaling in melanocytes. Nature 391:298-301.
Ito, M., Y. Kawa, H. Ono, M. Okura, T. Baba, Y. Kubao, S. I. Nishikawa, M. Mizoguchi, 1999. Removal of stem cell factor or addition of monoclonal anti-c-kit antibody induces apoptosis in murine melanocyte precursors. J. Invest. Dermatol. 112(5):796-801.
Jiang, X., O. Gurel, E. A. Mendiaz, G. W. Stearns, C. L. Clogston, H. S. Lu, T. D. Osslund, R. S. Syed, K. E. Langley, W. A. Hendrickson. 2000. Structure of the active core of human stem cell factor and analysis of binding to its receptor kit. EMBO J. 19:3192-3203.
Nishimura, E. K., S. A. Jordan, H. Oshima, H. Yoshida, M. Noriyama, I. J. Jackson, Y. Barrandon, Y. Miyachi, S. I. Nishikawa. 2002. Dominant role of the niche in melanocyte stem-cell fate determination. Nature 416:854-860.
Mager, M., R. Pause, N. Farjo, S. Muller-Rover, E. M. J. Peters, K. Foitzik, D. J. Tobin. 2004. Limitations of human occipital scalp hair follicle organ culture for studying the effects of minoxidil as a hair growth enhancer. Exp. Dermatol. 13:635-642.
Mol, C. D., K. B. Lim, V. Sridhar, H. Zou, E. Y. T. Chien, , B. C. Sang, J. Nowakowski, D. B. Kassel, , C. N. Cronin, D . E. McRee. 2003. Structure of a c-kit product complex reveals the basis for kinase transactivation. J. Biol. Chem. 278:31461-31464.
Panteleyev, A. A., C. A. B. Jahoda, A. M. Christiano. 2001. Hair follicle predetermination. J. Cell Sci. 114:3419-3431.
Peters, E. M. J., D. J. Tobin, N. Botchkareva, M. Maurer, R. Paus. 2002. Migration of melanoblasts into the developing murine hair follicle is accompanied by transient c-Kit expression. Histochem. Cytochem. 50:751-766.
Peters, E. M. J., M. Maurer, V. A. Botchkarev, K. deM. Jensen, P. Welker, G. A. Scott, R. Paus. 2003. Kit is expressed by epithelial cells in vivo. J. Invest. Dermatol. 121:976-984.

(Continued)

*Primary Examiner*—Bridget E Bunner
(74) *Attorney, Agent, or Firm*—Pai Patent & Trademark Law Firm; Chao-Chang David Pai

(57) ABSTRACT

The present invention provides comprehensive compositions for treating problems associated with hair graying and balding via the incorporation of: (i) the cell growth factor of HSCF to induce the migration of melanocyte stem cells and keratinocyte stem cells and then to increase the growth of melanocytes and keratinocytes in hair follicles, (ii) a formula of amino acids and vitamins to provide the nutritional factors for hair growth and pigmentation, and (iii) minoxidil to enhance the function of HSCF on hair re-growth. The compositions comprising at least one of (i), (ii) or (iii) are administered on skin and/or scalp through liposome in the follicular delivery systems, including penetration enhancers and suitable carrier bases. The compositions packaged in liposome in the follicular delivery systems in this invention has been proven to reach the dermis from the skin surface within 15-30 min.

12 Claims, 12 Drawing Sheets

OTHER PUBLICATIONS

Philpott, M. P., D. A. Sander, T. Kealey. 1994. Effects of insulin and insulin-like growth factors on cultured human hair follicles: IGF-I at physiologic concentrations is an important regulator of hair follicle growth in vitro. J. Invest. Dermatol. 102(6):857-861.

Sulaimon, S. S.,B. E. Kitchell. 2003. The biology of melanocytes. Vet. Dermatol. 14(2):57-65.

Zhang, Z., R. Zhang, A. Joachimiak, J. Schlessinger, X. P. Kong. 2000. Crystal structure of human stem cell factor: Implication for stem cell factor receptor dimerization and activation. Proc. Natl. Acad. Sci. USA 97:7732-7737.

Park, W. S., C. H. Lee, B. G. Lee, I. S. Chang. 2003. The extract of *Thujae occidentalis* semen inhibited 5α-reductase and androchronogenetic alopecia of B6CBAF1/j hybrid mouse. J. Dermatol. Sci. 31:91-98.

* cited by examiner (a)

M = protein marker
1 = pet24a-SCF/codon plus total cellular protein
2 = insoluble fraction of pet24a-SCF/codon plus cell lysate
3 = purified SCF protein (b)

SCF-Soluble  Western Blot

Condition :
    Mouse anti Human SCF monoclon antibody (1.5ug/ml)

Rabbit anti Mouse IgG (1:15000)

Post-transferred

Western blot

M = protein marker
1 = pet24a-IGF-1/codon plus total cellular protein
2 = insoluble fraction of pet24a-IGF-1/codon plus cell lysate
3 = purified IGF-1 protein M = protein marker
1 = pet24a-HSCF-II/codon plus total cellular protein
2 = insoluble fraction of pet24a-HSCF-II/codon plus cell lysate
3 = purified HSCF-II protein (a)

(b)

COMPOSITIONS AND METHODS FOR DUAL THERAPIES OF HAIR GRAYING AND BALDING IN FOLLICULAR DELIVERY SYSTEMS

CROSS-REFERENCE TO RELATED APPLICATIONS

This application claims the benefit of U. S. Provisional Application No. 60/735,925, filed Nov. 10, 2005, which is incorporated herein by reference.

INCORPORATION BY REFERENCE OF SEQUENCE LISTING

A sequence listing submitted as a text file via EFS-Web is incorporated Herein by reference. The text file containing the sequence listing is named "PB 050538F_Sequence _List_Final. txt"; its date of creation is Nov. 8, 2006; and its size is 10,855 bytes.

BACKGROUND OF THE INVENTION

1. Field of the Invention

The present invention provides comprehensive compositions for treating The problems associated with hair graying and balding via the incorporation of: (i) Cell growth factor of HSCF to induce the migration of melanocyte stem cells and keratinocyte stem cells and then to increase the growth of melanocytes and keratinocytes in hair follicles, (ii) a formula of amino acids and vitamins to provide the nutritional factors for hair growth and pigmentation, and (iii) minoxidil to enhance the function of HSCF on hair re-growth. The compositions comprising at least one of (i), (ii) or (iii) are administered on skin and/or scalp through the liposome in the follicular delivery systems, including penetration enhancers and suitable carrier bases. The composition packaged in liposome in the follicular delivery systems of this invention has been proven to reach the dermis from the skin surface within 15-30 min. The essential function of the liposome is to maintain the activity of the growth factor of HSCF for at least one to three years.

2. Description of the Prior Art

Dual therapies of hair graying and balding in topical delivery systems have never been claimed in the market. When a graying hair derives in large part from a mixture of pigmented and white hair, it can clearly be noted that individual hair follicles indeed exhibit pigment dilution or true graying. This dilution could be due to a reduction in tyrosinase activity of hair bulbar melanocytes, sub-optimal melanocyte-cortical keratinocyte interaction, or defective migration of melanocytes from a reservoir in the upper outer root sheath to the pigment-permitting microenvironment close to dermal papilla of the hair bulb[12]. Some studies have reported that stem cell factor (SCF) has the functions to proliferate and migrate to the melanoblasts and keratinoblasts restored in the upper outer root sheath, called hair bulge[1, 2]. These melanoblasts and keratinoblasts, called melanocyte and keratinocyte stem cells, respectively, in hair bulge, could proliferate and migrate to dermal papilla in hair bulb and then differentiate to become melanocytes and keratinocytes[12, 13, 14]. Hair pigmentation is mostly produced by melanin accumulation, which is secreted from melanocytes[12, 16]. And hair shaft is mostly produced by keratin accumulation, which is secreted from keratinocytes. This growth factor of SCF has been proven to stimulate stem cells in hair bulge[3, 6, 9]. However, mice with homozygous SCF gene mutation (SL⁻/SL⁻) show the symptoms of white hair, infertility, and anemia[1, 5]. It suggests the importance of SCF in hair pigmentation[7, 13], but effects on hair growth are limited because the mutated mice still have hair. In addition, many growth factors and signals through different pathways control the hair growth. Especially, insulin-like growth factor-I (IGF-I) has been reported to induce growth of hair in many papers[4, 15]. Based on our previous data, the same results have also been obtained. Although the amino acid sequence and protein structure of recombinant human SCF has been clearly studied[17] and also been applied as a patent (U.S. Patent Publication No.: 20050080250, application Ser. No. 10/620, 642, filed: Jul. 16, 2003. Methods of stimulating growth of stromal cells in a human.), SCF and other ingredients are incorporated to claim the dual therapies for hair aging in our experimental data.

The combination of the two growth factors, SCF and IGF-I, has been studied to have the more advanced functions on the hair follicles in our study, because it significantly stimulates the hair growth and melanin synthesis at the same time. We gave the definition of the two growth factors of SCF and IGF-I as HSCF (hair stem cell factor), meaning either the combination, named HSCF-I, or the recombinant protein, named HSCF-II. The recombinant protein of HSCF-II is first established by our group, which is produced by a cloning vector inserted with a combination of human SCF and IGF-I sequence together. The medium containing HSCF results in a higher increase of shaft length of mouse hair follicles cultured in vitro, when compared with SCF or IGF-I alone. After the above compositions are administered along with a hair follicular delivery vehicle and/or device on the skin of mice, longer hair length and darker pigmentation of hair shaft are obtained.

Minoxidil, being a potassium channel opener, has been proven to induce human hair growth from many papers and is popular in the market to treat patients with androgenic alopecia. But the effects of minoxidil on treating hair balding are still limited[10]. The functions of minoxidil could reduce continuous hair loss, but couldn't increase hair amount and density or recover the pigment of graying hair. We tried to amplify the function of minoxidil by adding the above compositions, because it has been proven by the inventors of this invention that HSCF could stimulate the stem cells in hair bulge to migrate into hair bulb, and then differentiate to melanocyte and keratinocyte to regenerate a newly pigmented hair in a hair follicle.

The results showed that compositions of (i) HSCF, (ii) a formula of some amino acids and vitamins, and (iii) minoxidil could achieve the best efficiency on hair growth and melanin synthesis. It also has been proven to treat the graying and balding problems by the in vitro culture of hair follicle organ and also by the in vivo animal models of graying and balding mice. The invention could be further applied to treat the hair aging of human beings.

REFERENCE

1. Broudy, V. C. (1997) Stem cell factor and hematopoiesis. Blood 90:1345-1364.
2. Botchkareva, N. V., M. Khlgatian, B. J. Longley, V. A. Botchkarev, B. A. Gilchrest, 2001. SCF/c-KIT signaling is required for cyclic regeneration of the hair pigmentation unit. FASEB J. 15(3):645-658.
3. Botchkareva, N. V., V. A. Botchkarev, B. A. Gilchrest. 2003. Fate of melanocytes during development of the hair follicle pigmentary unit. J. Investig. Dermatol. Symp. Proc. 8(1): 76-79.

4. Frankel, S. K., B. M. Moats-Staats, C. D. Cool, M. W. Wynes, A. D. Stiles, D. W. Riches. 2005. Human insulin-like growth factor-IA expression on transgenic mice promotes adenomatous hyperplasia but not pulmonary fibrosis. Am. J. Physiol. Lung Cll Mol. Physiol. 288(5):L805-812.

5. Guyonneau, L., F. Murisier, A. Rossier, A. Moulin, F. Beermann. 2004. Melanocytes and pigmentation are affected in dopachrome tautomerase knockout mice. Mol. Cell Biol. 24:3396-3403.

6. Hemesath, T. J., E. R. Price, C. Takemoto, T. Badalian, D. E. Fisher. 1998. MAP kinase links the transcription factor microphthalmia to c-kit signaling in melanocytes. Nature 391:298-301.

7. Ito, M., Y. Kawa, H. Ono, M. Okura, T. Baba, Y. Kubao, S. I. Nishikawa, M. Mizoguchi, 1999. Removal of stem cell factor or addition of monoclonal anti-c-kit antibody induces apoptosis in murine melanocyte precursors. J. Invest. Dermatol. 112(5):796-801.

8. Jiang, X., O. Gurel, E. A. Mendiaz, G W. Stearns, C. L. Clogston, H. S. Lu, T. D. Osslund, R. S. Syed, K. E. Langley, W. A. Hendrickson. 2000. Structure of the active core of human stem cell factor and analysis of binding to its receptor kit. EMBO J. 19:3192-3203.

9. Nishimura, E. K., S. A. Jordan, H. Oshima, H. Yoshida, M. Noriyama, I. J. Jackson, Y. Barrandon, Y. Miyachi, S. I. Nishikawa. 2002. Dominant role of the niche in melanocyte stem-cell fate determination. Nature 416:854-860.

10. Mager, M., R. Pause, N. Farjo, S. Muller-Rover, E. M. J. Peters, K. Foitzik, D. J. Tobin. 2004. Limitations of human occipital scalp hair follicle organ culture for studying the effects of minoxidil as a hair growth enhancer. Exp. Dermatol. 13:635-642.

11. Mol, C. D., K. B. Lim, V. Sridhar, H. Zou, E. Y. T. Chien, B. C. Sang, J. Nowakowski, D. B. Kassel, C. N. Cronin, D .E. McRee. 2003. Structure of a c-kit product complex reveals the basis for kinase transactivation. J. Biol. Chem. 278:31461-31464.

12. Panteleyev, A. A., C. A. B. Jahoda, A. M. Christiano. 2001. Hair follicle predetermination. J. Cell Sci. 114:3419-3431.

13. Peters. E. M. J., D. J. Tobin, N. Botchkareva, M. Maurer, R. Paus. 2002. Migration of melanoblasts into the developing murine hair follicle is accompanied by transient c-Kit expression. Histochem. Cytochem. 50:751-766.

14. Peters, E. M. J., M. Maurer, V. A. Botchkarev, K. deM. Jensen, P. Welker, G. A. Scott, R. Paus. 2003. Kit is expressed by epithelial cells in vivo. J. Invest. Dermatol. 121:976-984.

15. Philpott, M. P., D. A. Sander, T. Kealey. 1994. Effects of insulin and insulin-like growth factors on cultured human hair follicles: IGF-I at physiologic concentrations is an important regulator of hair follicle growth in vitro. J. Invest. Dermatol. 102(6):857-861.

16. Sulaimon, S. S.,B. E. Kitchell. 2003. The biology of melanocytes. Vet. Dermatol. 14(2):57-65.

17. Zhang, Z., R. Zhang, A. Joachimiak, J. Schlessinger, X. P. Kong. 2000. Crystal structure of human stem cell factor: Implication for stem cell factor receptor dimerization and activation. Proc. Natl. Acad. Sci. USA 97:7732-7737.

18. Park, W. S., C. H. Lee, B. G Lee, I. S. Chang. 2003. The extract of *Thujae occidentalis* semen inhibited 5α-reductase and androchronogenetic alopecia of B6CBAF1/j hybrid mouse. J. Dermatol. Sci. 31:91-98.

SUMMARY OF THE INVENTION

In a first aspect, the present invention provides the compositions for dual hair therapies for balding and graying. The best composition of (i) the recombinant growth factor of HSCF, (ii) a formula of some amino acids and vitamins, and (iii) minoxidil significantly increases the degree of hair pigmentation and the length of hair shaft, not only in in vivo but also in in vitro models. In the base formula (ii), the effects of the mixture of HSCF and minoxidil are much stronger than those of HSCF (i) or minoxidil (iii) alone. It provides strong evidence for the effects of these compositions and methods for dual therapies of hair graying and balding in the follicular delivery systems.

In the invention, each of the recombinant human growth factors, including SCF, IGF-I and HSCF-II, has been cloned, expressed, and purified (FIG. 1-6). The activities of these proteins have been tested in different cell lines, respectively (FIGS. 3, 5). The artificial recombinant protein of HSCF-II is first established in this invention by integrating the human SCF and IGF-I sequence together into the expressing vector. When the pET24a vector was inserted with the sequence of HSCF-II, the expressed protein also has the combined functions of both SCF and IGF-I. Moreover, it appears that the combined functions on hair follicles are even better than each of SCF and IGF-I (FIG. 7). The HSCF-II possesses the benefits of being efficient, economical, and convenient. The major functions of HSCF-II on hair follicles are to induce the proliferation of melanocyte stem cells and keratinocyte stem cells, their migration from the bulge to the hair bulb, and also their differentiation into melanocytes and keratinocytes. It could revitalize the hairless follicles to regenerate pigmented hair shaft (FIG. 8).

The graying animal model to mimic human hair graying is first established by our invention. It is derived from the hybrid of the C3H and BALB/C mice. The hybrid possessing the heterologous tyrosinase gene (Tyr+/Tyr−) appears in light brown color, which is the mimic to the genotype of aging human in hair follicles because of tyrosinase depletion. In fact, tyrosinase is the most important enzyme to produce melanin. If any reason causes the inactivation of tyrosinase during aging, the hair would lose its color and becomes gray. We used the whiting gel (containing 1-20% hydroquinone and 1-20% glycolic acid) on the dorsal skin of the hybrid to cause the inhibition of the tyrosinase activity. After 7 days of treatment, the hair color of the re-grown hair in the hybrid becomes white. Actually, it is very easy to observe the hair color from the graying animal model to check if these treatments indeed work. In fact, it has been proven in this invention. The compositions significantly change the hair color (FIG. 8) and increase the melanin level (FIG. 9) of the hair shaft in the graying animal model.

Minoxidil has been popular in the market to treat patients with androgenic alopecia for many years. It has been theoretically explained that minoxidil could be a potassium-ion channel opener on cell membrane to help with the entrance of amino acids and other nutrients. But the effects of minoxidil on treating hair balding are still limited because it can reduce continuous hair loss but not increase the hair amount, density, or the pigment of the graying hair. The compositions in this invention can indeed amplify the function of minoxidil, by the extra additions of the growth factor of HSCF and a formula of some amino acids and vitamins (FIG. 7 and FIG. 10d). The function of HSCF on hair follicles is to stimulate the proliferation and migration of stem cells. And the formula supports rich nutrients to hair follicles. Since the best combination consists of three parts, it enhances not only the pigmentation of graying hair but also the regeneration of hairless follicles.

To prove the therapeutic function of these compositions on hair balding, we established the androchronogenetic alopecia (AGA) animal model, which was modified from a paper by Park et al.[18]. It is derived from the hybrid of C57BL/6J female×CBA/J male, and is called B6CBAF1/j hybrid. It has been proved that hair loss of the female of the hybrid can be induced by the subcutaneous injection of testosterone (1-100 mg/mice/day) for 3 weeks. Thus, the AGA animal model is the human AGA mimic. From the in vivo data (FIG. 10), it strongly suggests that even HSCF alone has the function to improve hair re-growth in the AGA mice. Moreover, the combination of HSCF and minoxidil has more efficacy in treating hair loss in the AGA mice, which re-grows hair more quickly. The result also shows that the mixture has the best efficacy in the hair growth of the hair follicle cultured in vitro (FIG. 7). In summary, the effect of the mixture on hair re-growth in the follicles is significantly better than minoxidil alone.

These compositions which are topically applied to the graying and AGA animal models through the follicular delivery systems should be packaged in liposome to preserve their activities, especially for the HSCF protein. The follicular delivery systems include penetration enhancers and suitable carrier bases. The term "penetration enhancers" as used herein means a compound that facilitates the movement of substances into and/or through the epidermis of skin. Examples of penetration enhancers include, but are not limited to, lipids, lipoproteins, fatty acids and fatty alcohol, detergents, alcohols, glycols, mineral oils, liposome, and transdermal delivery vehicles or devices. And the term "suitable carrier" as used herein means a carrier suitable for the topical application to mammalian skin without causing undue toxicity, irritation, allergic response, and the like. The addition of penetration enhancers and suitable carrier bases in the follicular delivery systems contribute to the most effectiveness on the dermis through the topical applications. We have proven that the penetration rate is limited to 15-30 min to reach the dermis from the skin application by the liposome of the follicular delivery system. It showed on the immunofluorescence of the liposome (FIG. 11a), the sizes of which are limited to 50 nm-2 µm, and the frozen specimen of mice skin after 15-30 min of the topical application of the liposome packaged with these compositions (FIG. 11b).

In summary, the present invention provides the compositions and methods for dual therapies of hair graying and balding. The compositions comprise (i) the growth factor of HSCF, (ii) a formula of amino acids and vitamins, and (iii) minoxidil in the topical delivery systems. The invention also provides two experimental animal models for testing the functions of the compositions on hair graying and balding in vivo. The invention further relates to dual therapeutic methods useful for treating disorders of human hair graying and balding due to aging.

These features and advantages of the present invention will be fully understood and appreciated from the following detailed description in view of the accompanying Drawings.

DETAILED DESCRIPTION OF THE PREFERRED EMBODIMENT

Example 1

Materials and Methods (1). Expression and Purification of Human Stem Cell Factor (SCF)

A. Gene Construction

Figure 12:
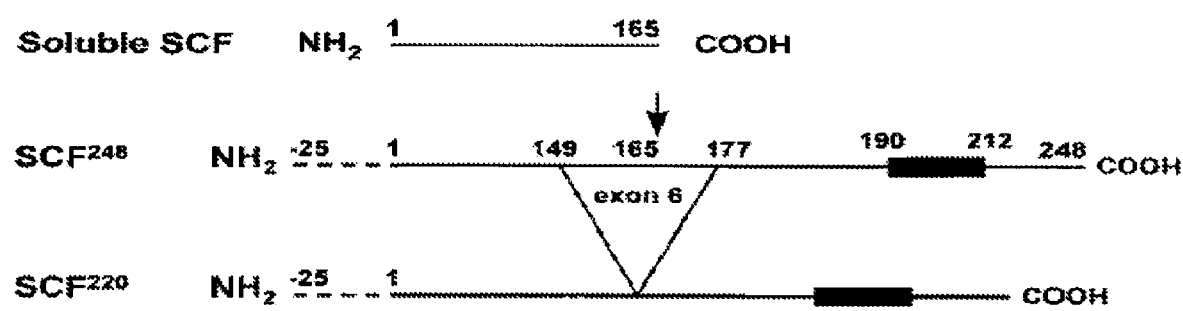
FIG. 12 shows the gene construction of three different stem cell factors (SCF).

SCF (kit ligand, mast cell growth factor, or steel factor) is encoded by the S1 locus on human chromosome 12q22-12q24. The soluble and Tran membrane forms of SCF are generated from the alternative splicing that includes or excludes a proteolytic cleavage site. Both the soluble and the transmembrane form of SCF are biologically active. SCF248 includes exon 6, which encodes a proteolytic cleavage site, resulting in the production of soluble SCF, which has 165 amino acids. The cleavage occurs after Ala. The lack of exon 6 in human SCF220 results in production of the transmembrane form of human SCF. In SCF220, amino acids 149-177 are replaced by a Gly residue. The three different SCF forms are illustrated in FIG. 12.

The soluble form of human SCF cDNA was obtained from the total RNA of human placenta by RT-PCR. The primers were designed as SEQ. ID NO:7 and SEQ ID NO:8 as Follows:

SCF primer:

F (BamHI):

5'cgggatccatgaagaagacacaaacttggattc 3' (SEQ ID NO: 7)

R (XhoI):

5'ccgctcgagaaccacacaatcactagtttcag 3' (SEQ ID NO: 8)

Figure 1:
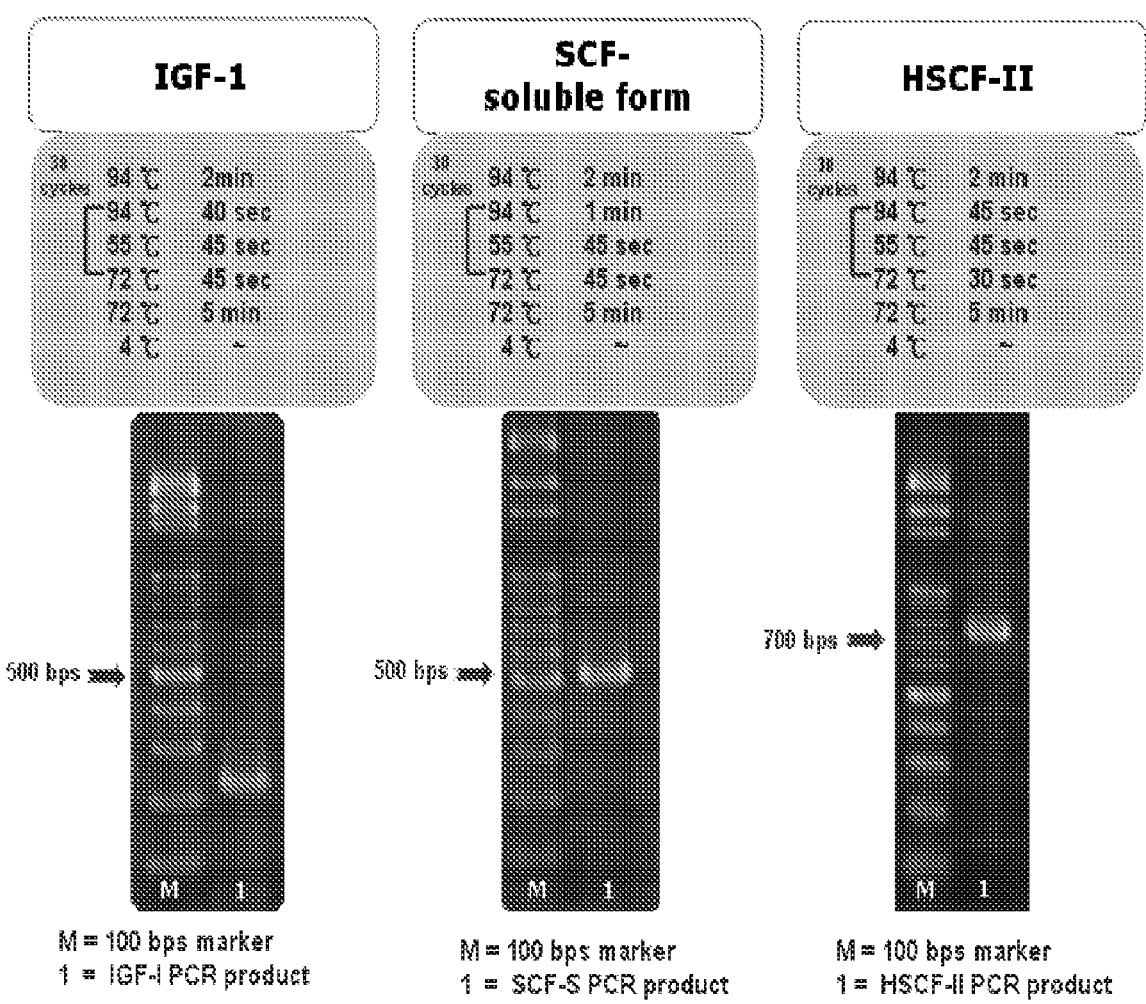
FIG. 1. The PCR products of human SCF, IGF-I, and HSCF-II.

The PCR cycles and products of SCF were described in FIG. 1. The nucleotide sequence of soluble SCF cDNA (495 bp) is set forth in SEQ ID NO:1. The 165 amino acids of soluble SCF are set forth in SEQ ID NO:2.

B. Protein Expression

Figure 2:
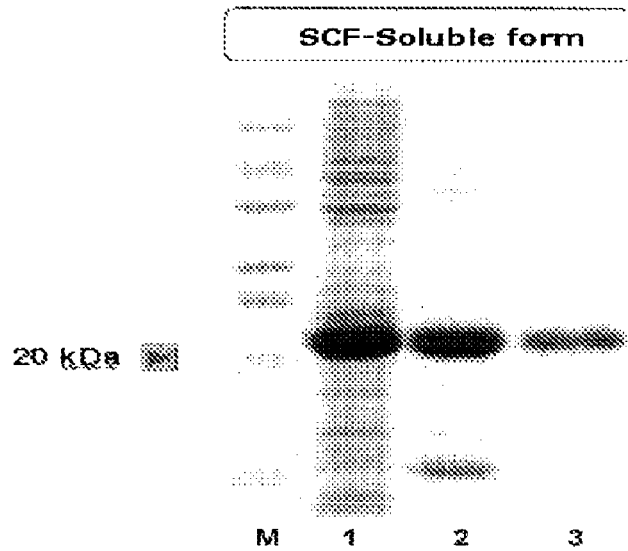
FIG. 2. The protein expression of soluble form of human SCF with results of SDS-PAGE shown in (a) and Western blot shown in (b).
Figure 2:
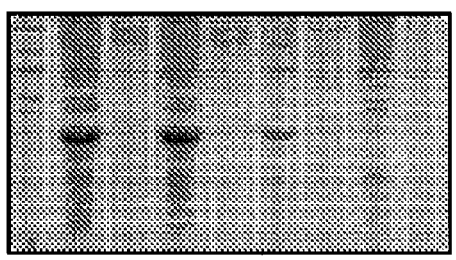
Figure 2:
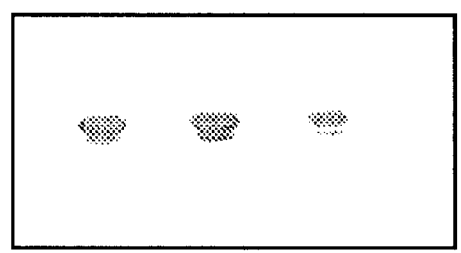

The protein expression of the soluble form of human SCF is shown as the results of SDS-PAGE and Western blot in FIG. 2.

C. Protein Purification

The pET24a-SCF was transformed into expression competent BL21-codon plus *E. coli* cells. The cells were grown in 5 ml LB containing 35 µg/ml kanamycin in a shaking incubator at 37☐ overnight. Then, 5 ml of the culture was added to 500 ml LB containing 35 µg/ml kanamycin and the culture was continued to grow in a 37° C. shaker for approximately 3 h until the OD550 reached 0.5-1. After the OD550 was around 0.5-1, protein expression was induced with isopropylthiogalactoside (IPTG) at concentration of 0.5 mM. After an incubation time of 6 h at 37° C., the cells were harvested by centrifugation and resuspended in 50 ml PBS containing 100 µg/ml lysozyme, pH 7.5. Store the suspension at 4° C. for 30 min. And then, the suspension were sonicated on ice (15×1.5 s pulses with 1 s intervals) and centrifuged for 10 min at 10000 g. The precipitate was resuspended in 50 ml IB wash buffer (20 mM Tris-HCl, pH 7.5, 10 mM EDTA, 1% Triton X-100) and centrifuged again at 10000 g for 10 min. Repeat this step three times. The supernatant was decanted and the inclusion body-containing precipitate of pET24a-SCF /BL21 codon plus was suspended in 25 ml 8 M urea buffer containing 20 mM Tris-HCl, 0.5 M NaCl, pH 7.8. Store the suspension at 4° C. for overnight to dissolve the inclusion bodies. Residual insoluble matter was removed by centrifuging at 15000 g for 30 min. The protein suspension was loaded onto a His-Bind resin column. After loading the sample, the purified protein was eluted by elute buffer (8 M urea, 20 mM Tris-HCl, 0.5 M NaCl, 0.25 M imidazole, pH 7.8). The purified protein solution was diluted with 9 volumes of rapid refolding buffer (2.5 M urea, 20 mM Tris-HCl, 0.01 mM EDTA, 2 mM GSH, 0.2 mM GSSG, 0.02% sodium azide, 0.2 M arginine, pH 8.5). After 48 h at room temperature, the mixture was concentrated ten-fold by ultrafiltration, and dialyzed against 1000 ml of refolding buffer (20 mM Tris-HCl, 0.01 mM EDTA) containing a descending gradient of urea (2-0 M) at 4° C.

D. Activity Analysis

Figure 3:
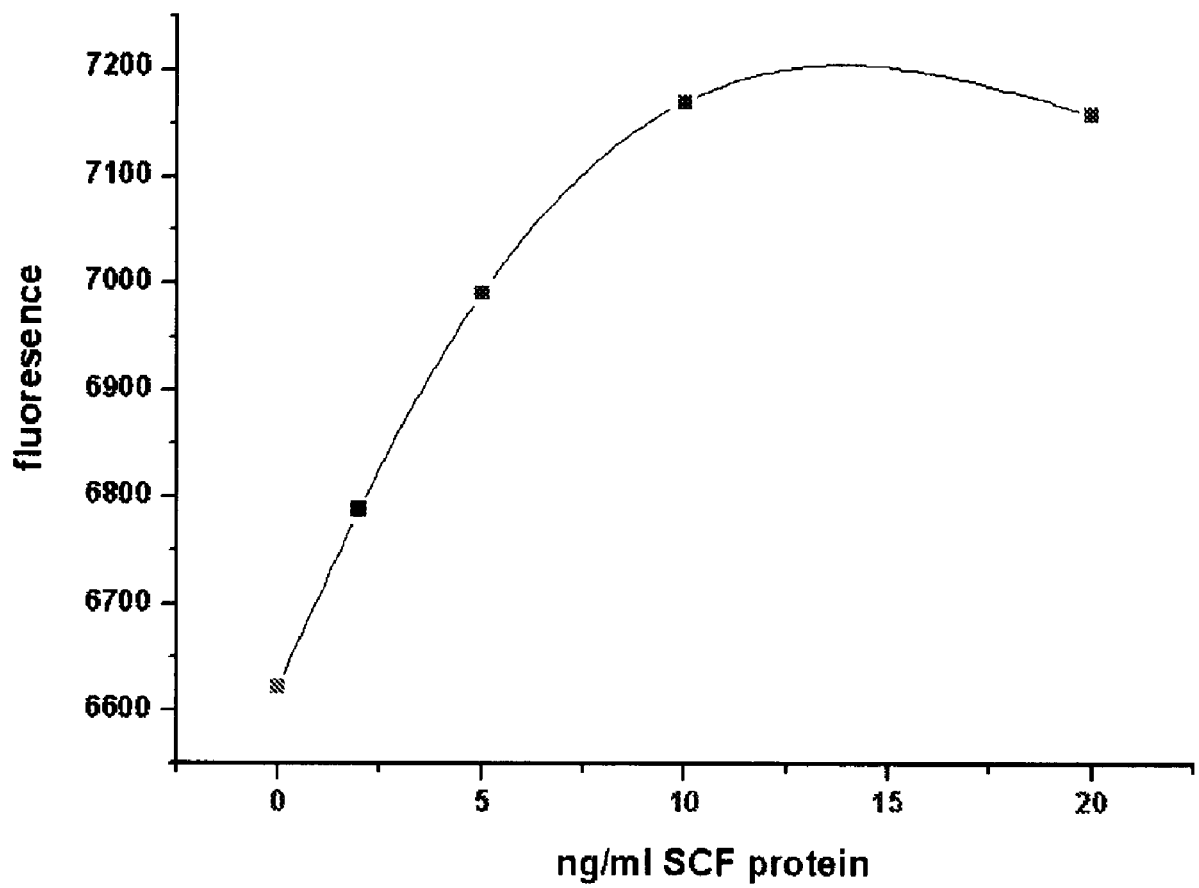
FIG. 3. The protein activity of SCF in the TF-I cell line.

The purified protein was prepared with PBS, 1 µl/well was transferred to microtiter plates mixed with 100 µl of TF-I cells (1×10$^4$ cells/ml), which had been washed three times with PBS and then re-suspended with RPMI 1640 medium containing 10% FCS and 0.08 ng/ml IL-3. The plates were incubated for 48 h, and then 10 µl of Alamarblue was added to each well, and incubated for another 4 h. After incubation, the fluorescence was monitored at 530-560 nm excitation wavelength and 590 nm emission wavelength. The assay of SCF activity in the TF-I cell line is shown in FIG. 3.

(2) Expression and Purification of Human Insulin-like Growth Factor-I (IGF-I)

A. Gene Construction

The 210 bp DNA sequence of human IGF-I cDNA was obtained from the total RNA of human placenta by RT-PCR. The primers were designed as SEQ ID NO:9 and SEQ ID NO:10 as follows:

IGF-I primer:

F (BamHI):

5' cgggatccggaccggagacgctctgcg 3'(SEQ ID NO: 9)

R (XhoI):

5' ccgctcgagagctgacttggcaggcttga 3'(SEQ ID NO: 10)

The PCR cycles and products of IGF-I were described in FIG. 1. The nucleotide sequence of human IGF-I cDNA (210 bp) is set forth in SEQ ID NO:3. The 70 amino acids of human IGF-I are set forth in SEQ ID NO:4.

B. Protein Expression

Figure 4:
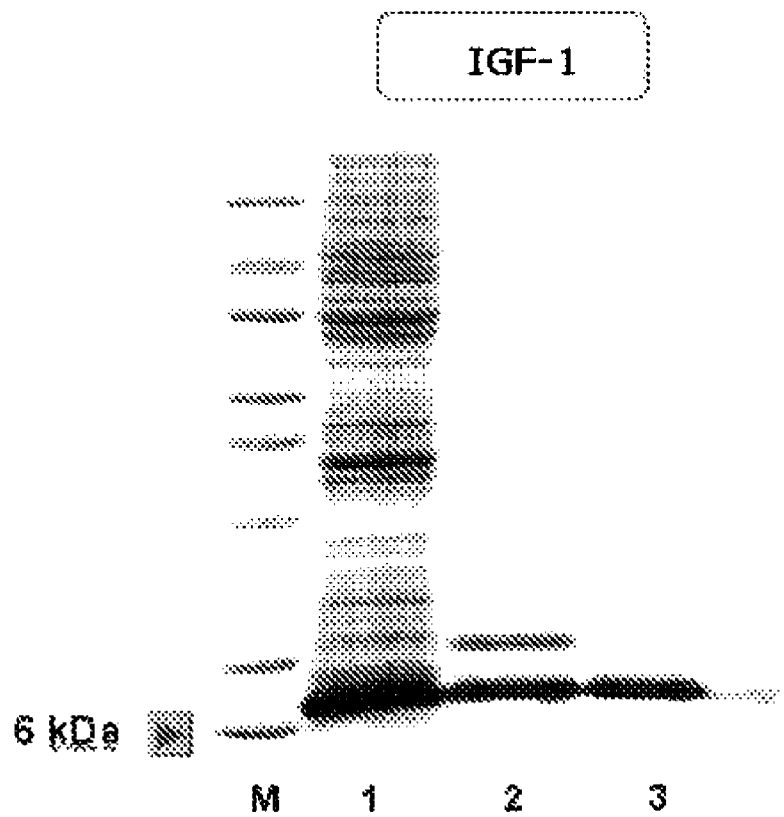
FIG. 4. The protein expression of human IGF-I. The result of SDS-PAGE is shown.

The protein expression of human IGF-I is shown as the result of SDS-PAGE in FIG. 4.

C. Protein Purification

The pET24a-IGF-I was transformed into expression competent BL21-codon plus *E. coli* cells. The cells were grown in 5 ml LB containing 35 µg/ml kanamycin in a shaking incubator at 37° C. overnight. Then, 5 ml of the culture was added to 500 ml LB containing 35 µg/ml kanamycin and the culture was continued to grow in a 37° C. shaker for approximately 3 h until the OD550 reached 0.5-1. After the OD550 was around 0.5-1, protein expression was induced with isopropylthiogalactoside (IPTG) at concentration of 0.5 mM. After an incubation time of 6 h at 37° C., the cells were harvested by centrifugation and resuspended in 50 ml PBS containing 100 µg/ml lysozyme, pH 7.5. Store the suspension at 4° C. for 30 min. And then, the suspension were sonicated on ice (15×1.5 s pulses with 1 s intervals) and centrifuged for 10 min at 10000 g. The precipitate was resuspended in 50 ml IB wash buffer (20 mM Tris-HCl, pH 7.5, 10 mM EDTA, 1% Triton X-100) and centrifuged again at 10000 g for 10 min. Repeat this step three times. The supernatant was decanted and the inclusion body-containing precipitate of pET24a-IGF-I/BL21 codon plus was suspended in 25 ml 8 M urea buffer containing 20 mM Tris-HCl, 0.5 M NaCl, pH 7.8. Store the suspension at 4° C. for overnight to dissolve the inclusion bodies. Residual insoluble matter was removed by centrifuging at 15000 g for 30 min. The protein suspension was loaded onto a His-Bind resin column. After loading the sample, the purified protein was eluted by elute buffer (8 M urea, 20 mM Tris-HCl, 0.5 M NaCl, 0.25 M imidazole, pH 7.8). The purified protein solution was diluted with 9 volumes of rapid refolding buffer (2.5 M urea, 20 mM Tris-HCl, 0.01 mM EDTA, 2 mM GSH, 0.2 mM GSSG, 0.02% sodium azide, 0.2 M arginine, pH 8.5). After 48 h at room temperature, the mixture was concentrated ten-fold by ultrafiltration, and dialyzed against 1000 ml of refolding buffer (20 mM Tris-HCl, 0.01 mM EDTA) containing a descending gradient of urea (2-0 M) at 4° C.

D. Activity Analysis

Figure 5:
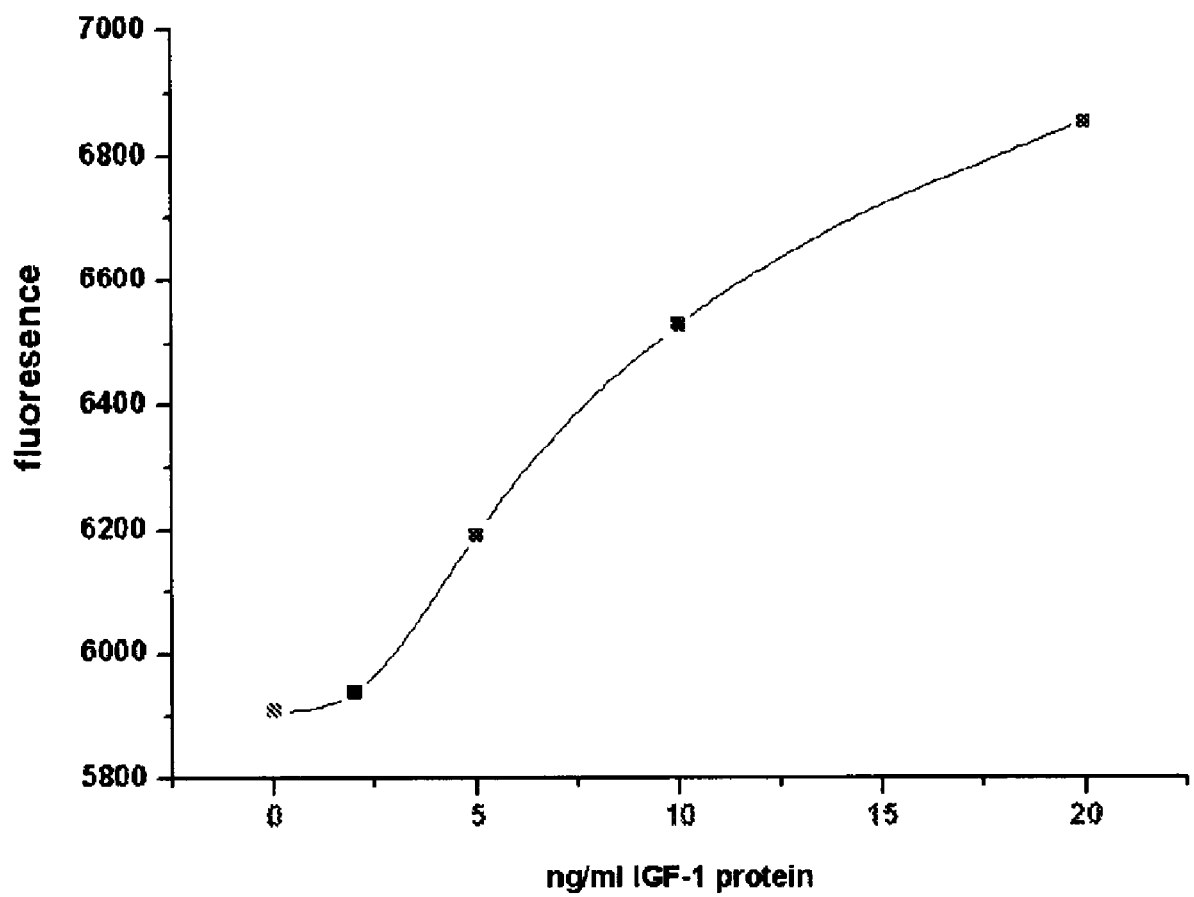
FIG. 5. The protein activity of IGF-I in the 3T3 cell line.

The sample was prepared with PBS, 1 µl/well was transferred to microtiter plates mixed with 100 µl of 3T3 cells (1×10$^4$ cells/ml), which had been washed three times with PBS then suspended with DMEM medium containing 1% FCS. The plates were incubated for 48 h, then 10 µl of Alamarblue was added to each well, and incubated for another 4 h. After incubating, the fluorescence was monitored at 530-560 nm excitation wavelength and 590 nm emission wavelength. The assay of IGF-I activity is shown in FIG. 5.

(3) Expression and Purification of Human Hair Stem Cell Factor-II (HSCF-II)

A. Gene Construction

The human hair stem cell factor-II (HSCF-II), which has never been reported before, is developed for the first time in our study. The 759-bp DNA sequence of HSCF-II, which is combined with human SCF of 510 bp, the linking peptide of 39 bp and IGF-I of 210 bp, is inserted into pET24a vector to express protein. The PCR cycles and products of HSCF-II were described in FIG. 1. The cDNA sequence of human HSCF-II is set forth in SEQ ID NO:5. The 253 amino acids of HSCF-II are set forth in SEQ ID NO:6.

B. Protein Expression

Figure 6:
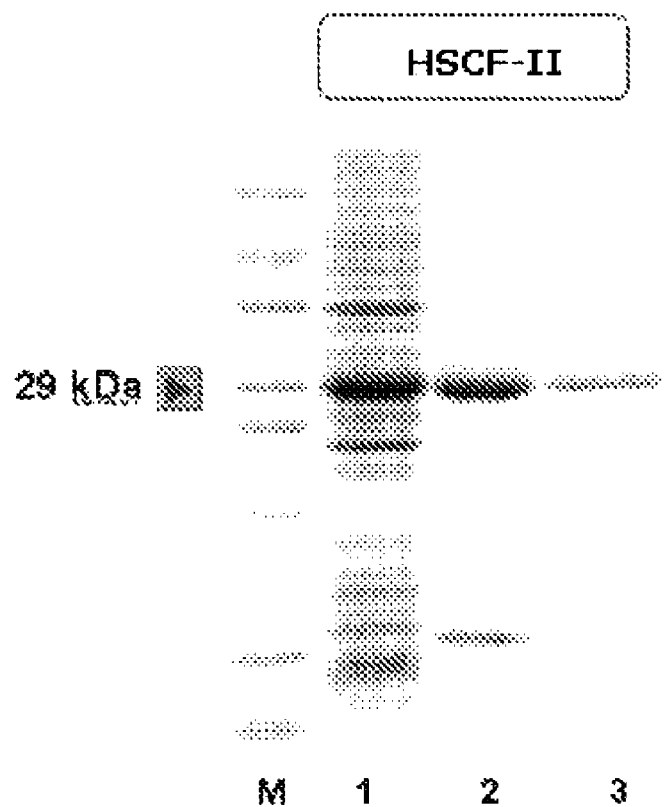
FIG. 6. The protein expression of the human HSCF-II is shown in SDS-PAGE.

The protein expression of the human HSCF-II is shown as the results of SDS-PAGE in FIG. 6.

C. Protein Purification

The pET24a-HSCF-II was transformed into expression competent BL21-codon plus *E. coli* cells. The cells were grown in 5 ml LB containing 35 μg/ml kanamycin in a shaking incubator at 37° C. overnight. Then, 5 ml of the culture was added to 500 ml LB containing 35 μg/ml kanamycin and the culture was continued to grow in a 37° C. shaker for approximately 3 h until the OD550 reached 0.5-1. After the OD550 was around 0.5-1, protein expression was induced with isopropylthiogalactoside (IPTG) at concentration of 0.5 mM. After an incubation time of 6 h at 37° C., the cells were harvested by centrifugation and resuspended in 50 ml PBS containing 100 μg/ml lysozyme, pH 7.5. Store the suspension at 4° C. for 30 min. And then, the suspension were sonicated on ice (15×1.5 s pulses with 1 s intervals) and centrifuged for 10 min at 10000 g. The precipitate was resuspended in 50 ml IB wash buffer (20 mM Tris-HCl, pH 7.5, 10 mM EDTA, 1% Triton X-100) and centrifuged again at 10000 g for 10 min. Repeat this step three times. And the inclusion body-containing precipitate of pET24a-HSCF-II/BL21 codon plus was suspended in 25 ml 6 M Gn-HCl buffer containing 20 mM Tris-HCl, 0.5 M NaCl, pH 7.8. Store the suspension at 4° C. for overnight to dissolve the inclusion bodies. Residual insoluble matter was removed by centrifuging at 15000 g for 30 min. The resulted protein solution was loaded onto a His-Bind resin column. After loading the sample, the purified protein was eluted by elute buffer (8 M urea, 20 mM Tris-Hcl, 0.5 M NaCl, 0.25 M imidazole, pH 7.8). The purified protein solution was diluted with 9 volumes of rapid refolding buffer (2.5 M urea, 20 mM Tris-HCl, 0.01 mM EDTA, 2 mM GSH, 0.2 mM GSSG, 0.02% sodium azide, 0.2 M arginine, pH 8.5). After 48 h at room temperature, the mixture was concentrated ten-folds by ultrafiltration, and dialyzed against 1000 ml of refolding buffer (20 mM Tris-HCl, 0.01 mM EDTA) containing a descending gradient of urea (2-0 M) at 4° C.

(4) The Preparation for Hair Follicle Organ Cultured in Vitro

Figure 7:
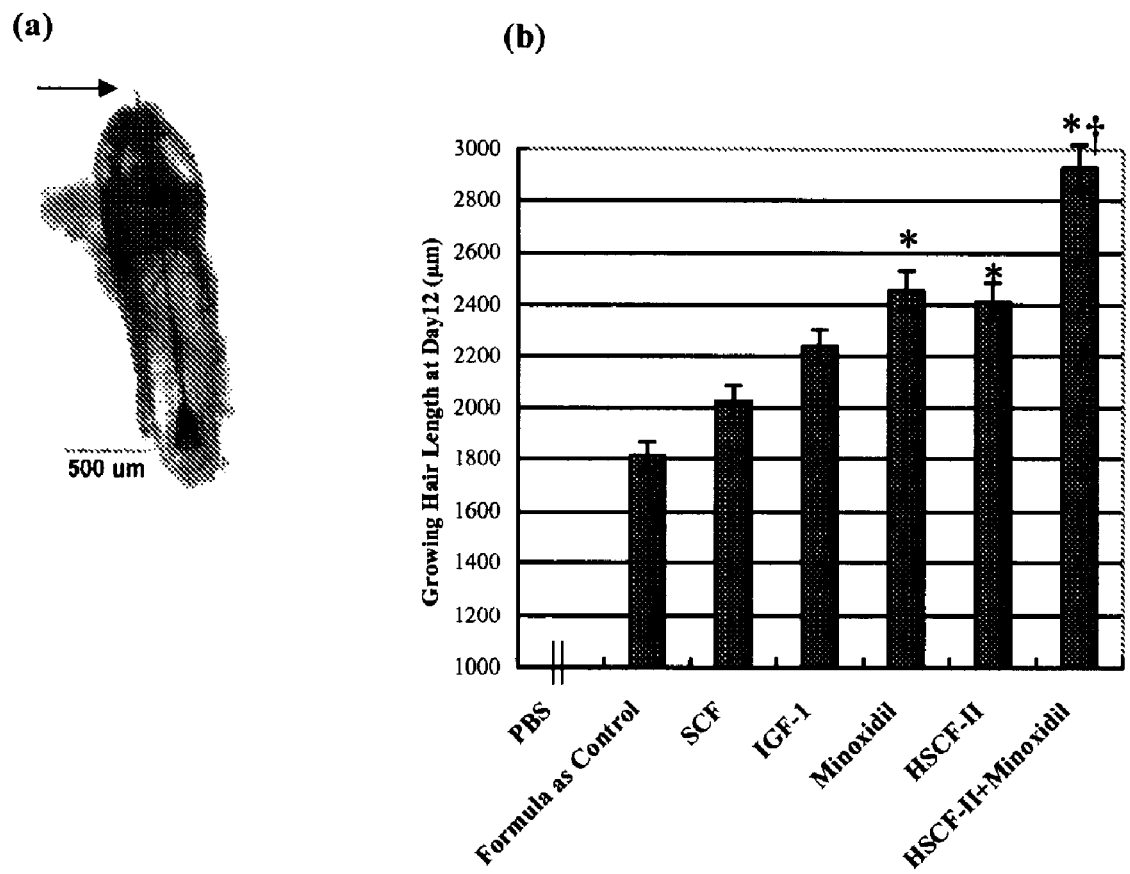
FIG. 7. The effect of IGF-I, SCF, HSCF and/or minoxidil on hair growth in vitro. (a) The whole follicle organ was dissected to culture and the length of the re-grown hair was measured from the top of the hair follicle as the beginning site (pointed by an arrow). (b) The data of hair length in the different treatments were shown. *Data of each treatment, compared with the positive control, is significantly different (P<0.05). †Data of each treatment, compared with the group of minoxidil, is significantly different (P<0.05).

At the age of 8 weeks, the F1 generation of C3H mated with BALB/C supplies the hair follicle material. By plucking the whiskers by depilating forceps, an anagen phase of the hair follicle can be induced. After three days of whisker plucking, the mice were killed and the hair follicle samples were harvested. Each selected hair follicle was then carefully isolated from the subcutaneous fat and the connective tissue surrounding the capsule was removed under a stereo-dissection microscope with fine forceps. We picked up the intact hair follicles with average size for the next step of culture, and which is in the early anagen stage, which is determined by the hair follicle conformation. Before culture, the hair fibre was first cut out at the surrounding line of the hair follicle to make the length measurement of hair growth much more easily in the future (FIG. 7).

Hair follicle were incubated at 37° C. in a water-saturated atmosphere of 5% $CO_2$ plus 95% air and cultured for 12 days in a 96 well-cell culture cluster (Falcon) containing 200 μl of cultural medium, supplemented with antibiotic penicillin 100 unit/ml-streptomycin 0.1 mg/ml (Sigma). The hair follicles were cultured in phosphate buffered saline (PBS, pH 7.4) as the negative control, containing NaCl 8 g/L, KCl 0.2 g/L, $Na_2HPO_4$ 1.44 g/L, and $KH_2PO_4$ 0.24 g/L. And the positive control was cultured in the formula of the control medium, containing some amino acids and vitamins, including 5-100 mg/L amino acids of alanine, arginine, asparagine, aspartic acid, cysteine, cystine, glutamic acid, glycine, histidine, isoleucine, leucine, lysine, methionine, phenylalanine, proline, serine, threonine, tryptophan, tyrosine, and valine; and 0.1-10 mg/L vitamins of ascorbic acid, biotin, pantothenate, choline chloride, ergocalciferol, folic acid, inositol, menadione sodium bisulfate, niacinamide, pyridoxal HCl, riboflavin, tocopherol, thiamine, vitamin A, and vitamin B12. The formula in the claim herein is briefly extended to the complex of any amino acid and vitamin.

There were several treatments, including SCF, IGF-I, HSCF, minoxidil alone, and the mixture of HSCF and minoxidil The ranges of these additional compositions in a formula were minoxidil 10-1000 μM, SCF 10-1000 ng/ml, IGF-I 1-1000 ng/ml, and HSCF 1-1000 ng/ml.

Ten hair follicles were cultured in each treatment. The cultured medium in each well was carefully removed every other day and replaced by the same compositions of the fresh medium. The length of the hair growth beginning from the cutting site was measured at Day 12. The whole procedure to compare the different treatments was repeated for 3 times.

Hair follicle was observed by the Inverted microscope (Lieca DM, IL) and captured with the image by CCD connecting with a computer. The hair length was analyzed with the computer software: Northern Eclipse image system. The data of hair length were analyzed with the Duncan's new multiple range test by one way analysis of variance (ANOVA) using the SigmaStat program (2002).

(5) The Graying Animal Model in Vivo

The graying animal model used to simulate human hair graying and to test the effects of the compositions on hair pigmentation in vivo, is established by the F1 generation. It is derived from the hybrid of the C3H and BALB/C mice, which grow white hair after the treatment with the whiting gel, containing 1-20% hydroquinone and 1-20% glycolic acid. In fact, tyrosinase has been proven to dominantly control the synthesis pathway of melanin. When human ages, the tyrosinase genes in melonocytes gradually become depleted, so white hair grows as a result. We establish a kind of mice with the heterologous tyrosinase gene (Tyr+/Tyr−), the activity of which is easy to inhibit by the treatment of whiting agent like hydroquinone. The BALB/C mice is in white color because of homologous depletion of tyrosinase gene (Tyr−/Tyr−) and the C3H strain with (Tyr+/Tyr+) appear in brown color. Heterologous tyrosinase gene (Tyr+/Tyr−) of the F1 generation is to simulate the genotype of human aging in hair follicles, which is much easier to induce tyrosinase depletion or inactivation to appear in white color. After the treatment with the whiting gel for 7 days, the F1 generation starts to grow white hair. If the treatment with HSCF makes the hair darker on the graying animal model, it could have the similar effect on the graying hair of human beings. There were three groups in this experiment, including the untreated group of the wild type as the negative control (without the whiting gel and without liposome), the positive control treated with the whiting gel and the liposome packaged with phosphate buffered saline (PBS), and the treated group of HSCF, which was treated with the whiting gel followed by the functional liposome of HSCF (1-200 µg/ml). There were six mice in each group at total three numbers of repeating times. Before the topical application, the dorsal hair (about 2×2 cm² area on skin) has been depilated carefully with fine forceps at Day 0. At Day 2, each mouse was treated with the whiting gel (containing 1-20% hydroquinone and 1-20% glycolic acid) once a day at p.m. for only one week. At the same time, it was also treated with 50 µl of the liposome onto the depilating area once a day at a.m. for two weeks, which duration is one week longer than the application of whiting gel.

In order to analysis the melanin level in the hair fibre, two mg of dorsal hair of each treatment was shaved and cut into small fragments. Then, each hair sample was dissociated by 1 M NaOH 1 ml and heated at 85° C. about 4 h, in order to dissociate the membrane of melanosome to release melanin. It should be protected from light. The colorful aqua from hair dissolution could be used for the melanin detection by spectrophotometer at OD 475 nm. The standard curve of melanin is measured at first by the commercial product of melanin.

(6) The AGA Animal Model in Vivo

Figure 10:
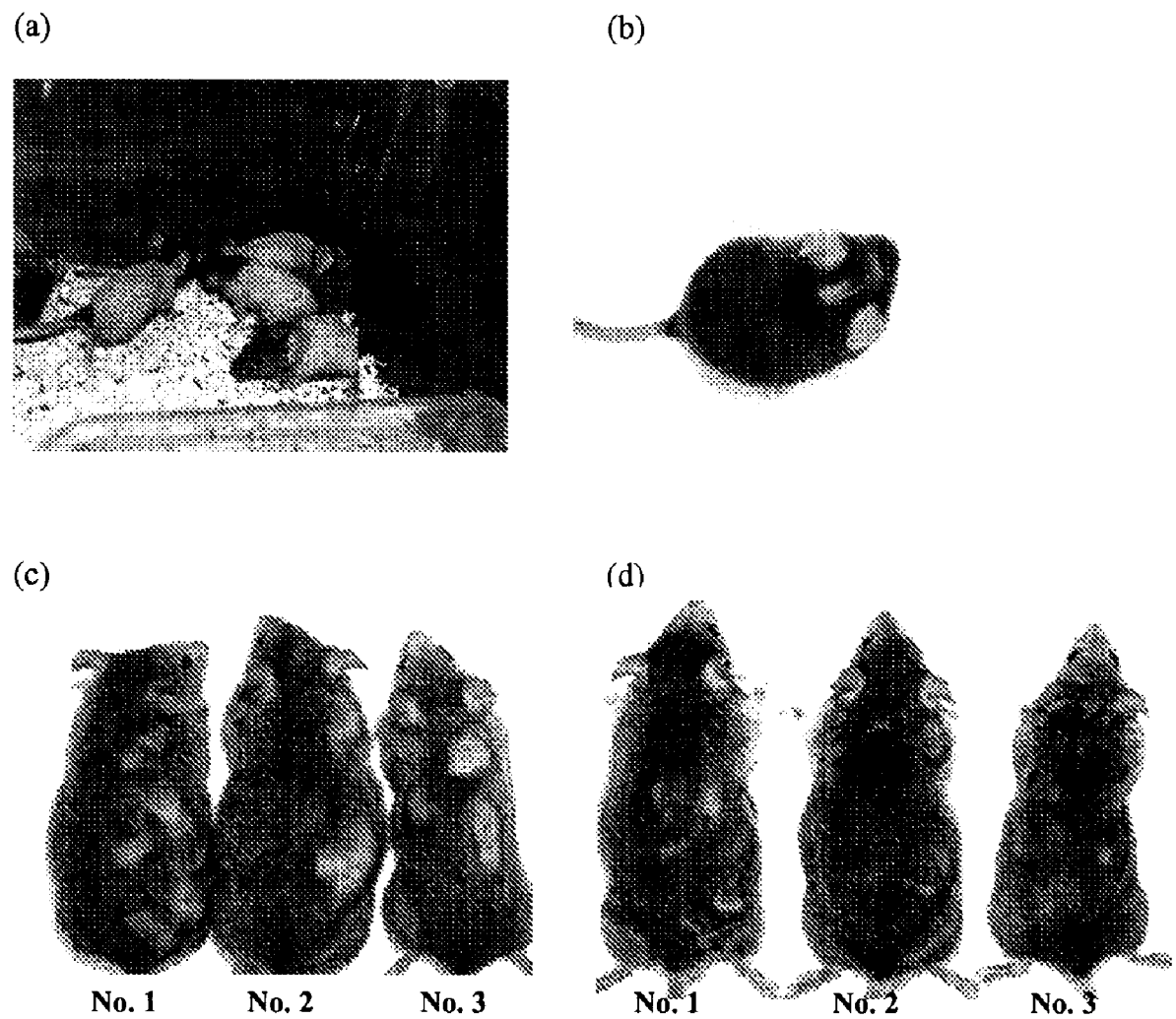
FIG. 10. The mutant C57BL/6J with jb/jb is shown before weaning (a) and after weaning (b). The AGA animal model is shown before treatment (c) and after 14 days of the treatment (d). The numbers indicate different treatments: No. 1 is the balding mice of the control, No. 2 is the balding mice treated with HSCF and minoxidil, and No. 3 is the balding mice treated with HSCF alone.

The spontaneous mutation of C57BL/6J mouse in our lab has an appearance of hair balding with homologous jb/jb genes (FIG. 10). We chose the mutant mice as the female parent. The androchronogenetic alopecia (AGA) animal model was then established by the hybrid of C57BL/6J female×CBA/J male. This hybrid is called the B6CBAF1/j hybrid mouse. It has been proved that hair loss can be induced for the female of the hybrid by the subcutaneous injection of testosterone (1 mg/mice/day) for 3 weeks. The female of the hybrid is more sensitive to testosterone than male mice, and therefore is appropriate for use as the human AGA balding mimic[18].

(7) The Penetration Rate of the Liposome in the Folliclular Delivery System

Figure 11:
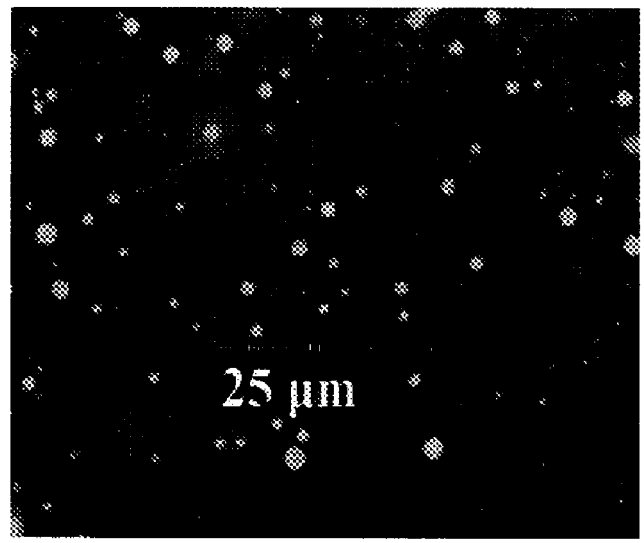
FIG. 11. It shows the particle size of liposome packaged with HSCF (a) and the penetration rate into the dermis (b) after 15-30 min of the topical application with immunofluorescence staining.
Figure 11:

In order to confirm the penetration and distribution of the follicular delivery system into dermis, we took the dorsal skin of mice after the topical application of the liposome containing HSCF. After 15-30 min of application, skin samples were embedded with the compound of Optimal Cutting Temperature (OCT, Tissue-Tek, 4583), frozen and sectioned at 8 µm thickness. Then, the sample was fixed with 4% paraformaldehyde, and blocked with 0.5% slim milk overnight at 4° C. for immunohistochemistry (FIG. 11). In order to label the liposome containing HSCF-II, the primary antibody rabbit anti-SCF (stem cell factor) (1:500) was used (PeproTech). The secondary antibody was florescence (FITC)-conjugated goat anti-rabbit IgG (1:1000) (Jackson ImmunoReasearch).

(8) The Stability of Growth Factor Activity in Liposome

In order to prove the maintenance of the activity of the growth factor HSCF in liposome, we used the reporter protein, enhanced green fluorescence protein (EGFP), to mix with HSCF together in liposome which were stored at the 37° C. incubator for three years. And then, the liposome was checked for the green fluorescence of EGFP to prove the activity of HSCF under the fluorescence microscopy every month. It showed that the protein activity of EGFP could last more than one to three years at 37° C.

Example 2

Effect of HSCF, the Formula and Minoxidil on Hair Growth in Vitro Culture

The hair follicle organs were completely dissected and cultured in vitro to test the effects of the different compositions on the hair re-growth. The results shown in FIG. 7 suggest that the best significant effect of the treatment on the hair re-growth is obtained from the mixture of HSCF, the formula and minoxidil. When hair follicles were cultured in the phosphate buffer solution (PBS), they didn't grow at all. In fact, the hair re-growth effect of HSCF is better than that of SCF and IGF-I each. It indeed proves the effect of HSCF on the hair growth. Moreover, it strongly suggests that the mixture of HSCF and minoxidil is better than minoxidil or HSCF alone ($P<0.05$).

The ranges of these compositions in a formula were minoxidil 10-1000 µM, SCF 10-1000 ng/ml, IGF-I 1-1000 ng/ml, and HSCF 1-1000 ng/ml. The formula of the cultural medium contains some amino acids and vitamins, including 5-100 mg/L each of amino acids of alanine, arginine, asparagine, aspartic acid, cysteine, cystine, glutamic acid, glycine, histidine, isoleucine, leucine, lysine, methionine, phenylalanine, proline, serine, threonine, tryptophan, tyrosine, and valine; and 0.1-10 mg/L each of vitamins of ascorbic acid, biotin, pantothenate, choline chloride, ergocalciferol, folic acid, inositol, menadione sodium bisulfate, niacinamide, pyridoxal HCl, riboflavin, tocopherol, thiamine, vitamin A, and vitamin B12.

Example 3

Figure 8:
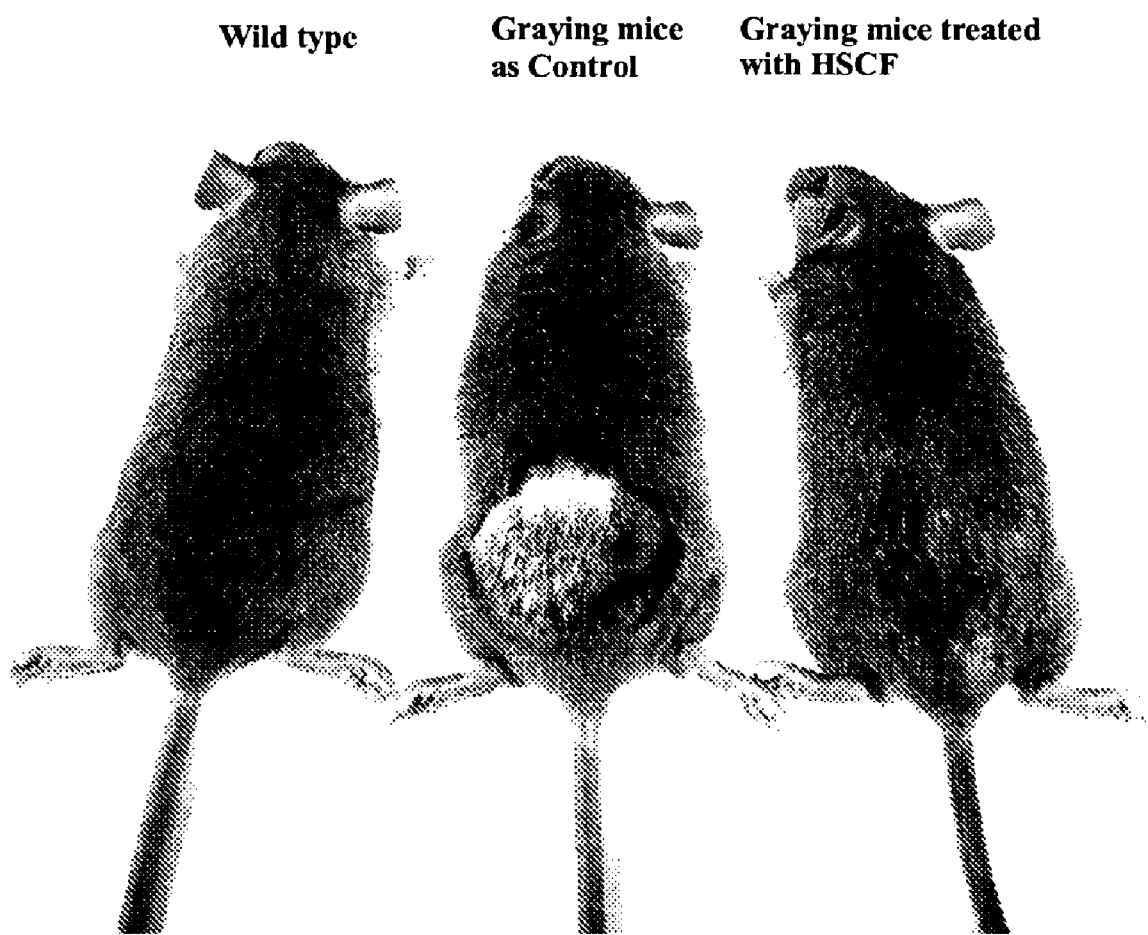
FIG. 8. The effect of HSCF on the hair color of the graying animal model. The dorsal hair color after the treatment was much darker than the control and similar to the wild type.
Figure 9:
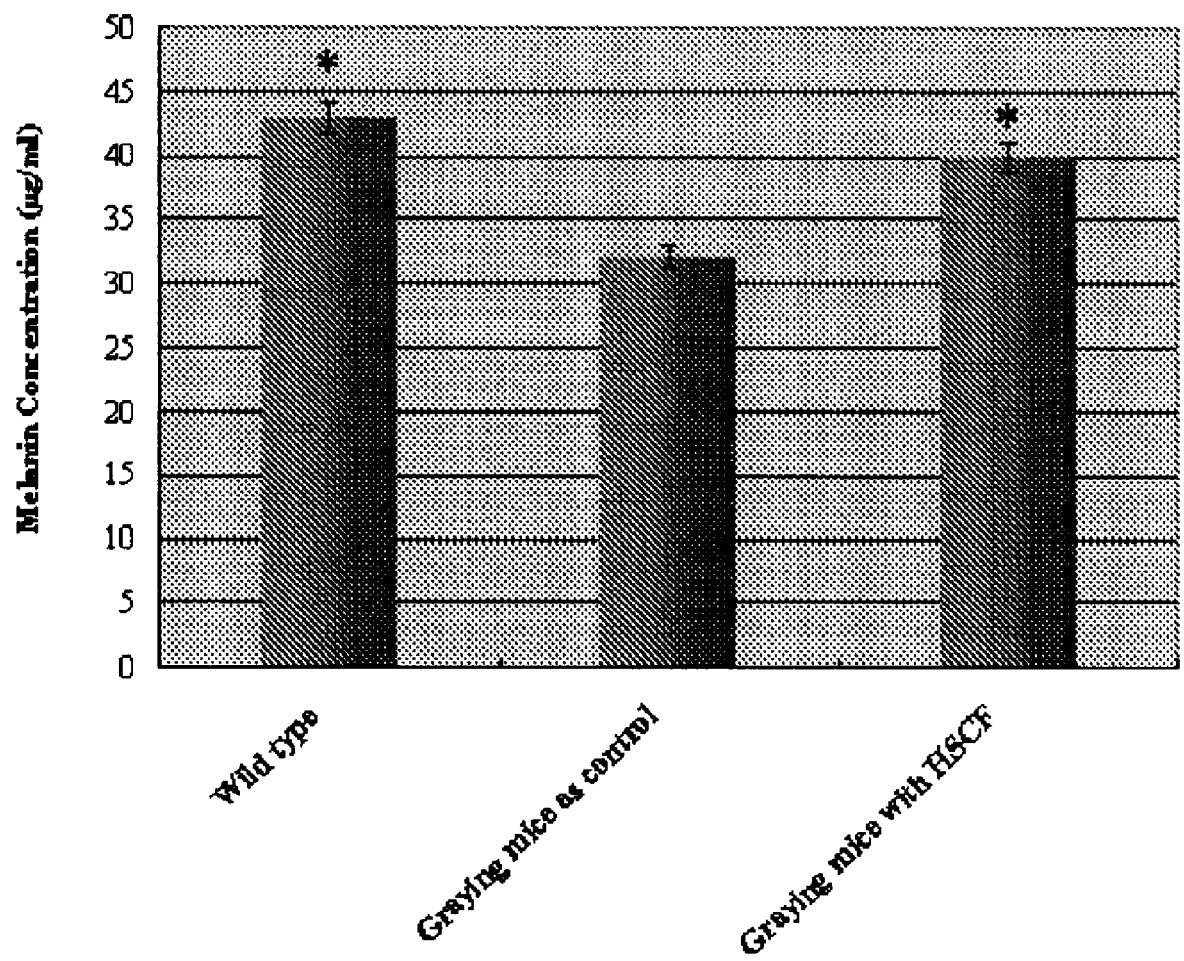
FIG. 9. The effect of HSCF on the melanin synthesis of the re-grown hair on the graying animal model. The symbol * means a statistically significant difference, when compared with the control to be significant (P<0.05).

Topical Application of HSCF for Hair Melanin Synthesis on the Graying Animal Model Based on the function of HSCF on melanocyte stem cells, we chose the graying animal model to test the therapeutic effect of HSCF on hair graying through topical application. The HSCF protein was packaged in liposome and applied on the dorsal skin through the topical application of the follicular delivery system. The results showed that the hair color of the treated group appeared much darker than the graying mice of the control (FIG. 8). The pigment in the hair shaft was then tested for the content of melanin. It also showed that the content of melanin is higher in this treated group ($P<0.05$), as well as in the wild type (FIG. 9). It proves the therapeutic effect of HSCF in the claims on the recovery of the pigment in the graying hair.

Example 4

Topical Application of HSCF and Minoxidil for Hair Regeneration on the AGA Animal Model Based on the function of HSCF on keratinocyte stem cells, we chose the AGA animal model to test the therapeutic effect of HSCF on hair loss through topical application. The HSCF protein was packaged in liposome and applied on the dorsal skin through the topical application of the follicular delivery system. The results showed that the hairless follicles re-grew new hair more quickly in the mice treated with HSCF and/or minoxidil than in the balding mice of the control (FIG. 10). Although the effect of HSCF alone is enough to stimulate the hair growth, it is recommended that minoxidil be combined with HSCF to heal the hair balding. The invention proves the therapeutic effect of HSCF in the claims on the hair re-growth of baldness and the even more effective effect of HSCF combined with minoxidil in the claims on the balding therapy.

Example 5

Liposome in the Follicular Delivery systems

In the study, we test the extent of deposition of the compositions containing the HSCF, the formula of amino acids and vitamins, and minoxidil into the hair follicles of the graying mice model and AGA mice model following a topical liposome-application in the follicular delivery systems. The follicular delivery systems include penetration enhancers and suitable carrier bases and/or devices. The term "penetration enhancer" as used herein means a compound that facilitates the movement of substances into and/or through the epidermis of skin. Examples of penetration enhancers include, but are not limited to, lipids, lipoproteins, fatty acids and fatty alcohol, detergents, alcohols, glycols, mineral oils, liposome, a trans-dermal delivery vehicle or device. And the term "suitable carrier" as used herein means a carrier suitable for topical application to mammalian skin without causing undue toxicity, irritation, allergic response, and the like. The addition of penetration enhancers and suitable carrier bases in the mixture contributes to the effectiveness of topical delivery system on hair follicles.

The HSCF packaged in liposome in the follicular delivery systems in this invention has been proven to reach the dermis from the skin surface within 15-30 min (FIG. 11b). The essential function of the liposome could maintain the activity of the growth factors for at least 1-3 years, because the green fluorescence of EGFP in the liposome could be detected under the fluorescence microscope for 1-3 years (FIG. 11a).

Many changes and modifications in the embodiments of the invention described above can, of course, be carried out without departing from the scope thereof. Accordingly, to promote the progress in science and the useful arts, the invention is disclosed and is intended to be limited only by the scope of the appended claims.

---

What is claimed is:

1. An isolated recombinant polynucleotide comprising the nucleotide sequence set forth in SEQ ID NO:5.

2. The isolated recombinant polynucleotide of claim 1, which is obtained by recombination of the nucleotide sequence set forth in SEQ ID NO:1 and the nucleotide sequence set forth in SEQ ID NO:3.

3. An isolated polypeptide comprising the amino acid sequence as set forth in SEQ ID NO:6.

4. The isolated polypeptide of claim 3, which is produced by combining human SCF (SEQ ID NO:2) and IGF-I (SEQ ID NO:4).

5. The isolated polypeptide of claim 3, which is a recombinant polypeptide produced by inserting a combination of SEQ ID NO:1 and SEQ ID NO:3 into expression vector of pET24a.

6. A medicinal composition, comprising hair stem cell factor (HSCF) as set forth in SEQ ID NO:6, a plurality of amino acids, a plurality of vitamins, and minoxidil.

7. The medicinal composition of claim 6, wherein the plurality of amino acids includes all 20 known amino acids.

8. The medicinal composition of claim 6, wherein the plurality of vitamins includes ascorbic acid, biotin, pantothenate, choline chloride, ergocalciferol, folic acid, inositol, menadione sodium bisulfate, niacinamide, pyridoxal HCl, riboflavin, tocopherol, thiamine, vitamin A, and vitamin B12.

9. A method of treating alopecia and hair graying, comprising:
   (a) packaging the medicinal composition of claim 6 with at least one penetration enhancer and at least one carrier base in a liposome; and
   (b) topically applying the liposome obtained in (a) on skin or scalp to thereby treat alopecia and hair graying.

10. The method of treating alopecia and hair graying of claim 9, wherein the at least one carrier base is selected from a group consisting of phospholipid, lethicin, cholesterol, PE, PEG, Tween 20, Tween 80, and Triton X-100.

11. A method of treating hair graying, comprising:
   (a) packaging the medicinal composition of claim 6 with at least one penetration enhancer and at least one carrier base in a liposome; and
   (b) topically applying the liposome obtained in (a) on skin or scalp to thereby treat hair graying.

12. The method of treating hair graying of claim 11, wherein the at least one carrier base is selected from a group consisting of phospholipid, lethicin, cholesterol, PE, PEG, Tween 20, Tween 80, and Triton X-100.

\* \* \* \* \*

SEQUENCE LISTING

```
<160> NUMBER OF SEQ ID NOS: 6

<210> SEQ ID NO 1
<211> LENGTH: 495
<212> TYPE: DNA
<213> ORGANISM: Human Soluble SCF (stem cell factor)
<220> FEATURE:
<221> NAME/KEY: CDS
<222> LOCATION: 1..495

<400> SEQUENCE: 1 atg aag aag aca caa act tgg att ctc act tgc att tat ctt cag      45
Met Lys Lys Thr Gln Thr Trp Ile Leu Thr Cys Ile Tyr Leu Gln
1               5                   10                  15 ctg ctc cta tct aat cct ctc gtc aaa act gaa ggg atc tgc agg      90
Leu Leu Leu Ser Asn Pro Leu Val Lys Thr Glu Gly Ile Cys Arg
                20                  25                  30 aat cgt gtg act aat aat gta aaa gac gtc act aaa ttg gtg gca     135
Asn Arg Val Thr Asn Asn Val Lys Asp Val Thr Lys Leu Val Ala
            35                  40                  45 aat ctt cca aaa gac tac atg ata acc ctc aaa tat gtc ccc ggg     180
Asn Leu Pro Lys Asp Tyr Met Ile Thr Leu Lys Tyr Val Pro Gly
        50                  55                  60 atg gat gtt ttg cca agt cat tgt tgg ata agc gag atg gta gta     225
Met Asp Val Leu Pro Ser His Cys Trp Ile Ser Glu Met Val Val
    65                  70                  75 caa ttg tca gac agc ttg act gat ctt ctg gac aag ttt tca aat     270
Gln Leu Ser Asp Ser Leu Thr Asp Leu Leu Asp Lys Phe Ser Asn
            80                  85                  90 att tct gaa ggc ttg agt aat tat tcc atc ata gac aaa ctt gtg     315
Ile Ser Glu Gly Leu Ser Asn Tyr Ser Ile Ile Asp Lys Leu Val
                95                  100                 105 aat ata gtg gat gac ctt gtg gag tgc gtg aaa gaa aac tca tct     360
Asn Ile Val Asp Asp Leu Val Glu Cys Val Lys Glu Asn Ser Ser
            110                 115                 120 aag gat cta aaa aaa tca ttc aag agc cca gaa ccc agg ctc ttt     405
Lys Asp Leu Lys Lys Ser Phe Lys Ser Pro Glu Pro Arg Leu Phe
        125                 130                 135 act cct gaa gaa ttc ttt aga att ttt aat aga tcc att gat gcc     450
Thr Pro Glu Glu Phe Phe Arg Ile Phe Asn Arg Ser Ile Asp Ala
```

```
                   140                 145                 150
ttc aag gac ttt gta gtg gca tct gaa act agt gat tgt gtg gtt              495
Phe Lys Asp Phe Val Val Ala Ser Glu Thr Ser Asp Cys Val Val
                   155                 160                 165

<210> SEQ ID NO 2
<211> LENGTH: 165
<212> TYPE: PRT
<213> ORGANISM: Human Soluble SCF

<400> SEQUENCE: 2

Met Lys Lys Thr Gln Thr Trp Ile Leu Thr Cys Ile Tyr Leu Gln
  1               5                  10                  15

Leu Leu Leu Ser Asn Pro Leu Val Lys Thr Glu Gly Ile Cys Arg
                 20                  25                  30

Asn Arg Val Thr Asn Asn Val Lys Asp Val Thr Lys Leu Val Ala
                 35                  40                  45

Asn Leu Pro Lys Asp Tyr Met Ile Thr Leu Lys Tyr Val Pro Gly
                 50                  55                  60

Met Asp Val Leu Pro Ser His Cys Trp Ile Ser Glu Met Val Val
                 65                  70                  75

Gln Leu Ser Asp Ser Leu Thr Asp Leu Leu Asp Lys Phe Ser Asn
                 80                  85                  90

Ile Ser Glu Gly Leu Ser Asn Tyr Ser Ile Ile Asp Lys Leu Val
                 95                 100                 105

Asn Ile Val Asp Asp Leu Val Glu Cys Val Lys Glu Asn Ser Ser
                110                 115                 120

Lys Asp Leu Lys Lys Ser Phe Lys Ser Pro Glu Pro Arg Leu Phe
                125                 130                 135

Thr Pro Glu Glu Phe Phe Arg Ile Phe Asn Arg Ser Ile Asp Ala
                140                 145                 150

Phe Lys Asp Phe Val Val Ala Ser Glu Thr Ser Asp Cys Val Val
                155                 160                 165

<210> SEQ ID NO 3
<211> LENGTH: 210
<212> TYPE: DNA
<213> ORGANISM: Human IGF-I
<220> FEATURE:
<221> NAME/KEY: CDS
<222> LOCATION: 1..210

<400> SEQUENCE: 3 gga ccg gag acg ctc tgc ggg gct gag ctg gtg gat gct ctt cag              45
Gly Pro Glu Thr Leu Cys Gly Ala Glu Leu Val Asp Ala Leu Gln
  1               5                  10                  15 ttc gtg tgt gga gac agg ggc ttt tat ttc aac aag ccc aca ggg              90
Phe Val Cys Gly Asp Arg Gly Phe Tyr Phe Asn Lys Pro Thr Gly
                 20                  25                  30 tat ggc tcc agc agt cgg agg gcg cct cag aca ggc atc gtg gat              135
Tyr Gly Ser Ser Ser Arg Arg Ala Pro Gln Thr Gly Ile Val Asp
                 35                  40                  45 gag tgc tgc ttc cgg agc tgt gat cta agg agg ctg gag atg tat              180
Glu Cys Cys Phe Arg Ser Cys Asp Leu Arg Arg Leu Glu Met Tyr
                 50                  55                  60 tgc gca ccc ctc aag cct gcc aag tca gct                                  210
Cys Ala Pro Leu Lys Pro Ala Lys Ser Ala
                 65                  70
```

<210> SEQ ID NO 4
<211> LENGTH: 70
<212> TYPE: PRT
<213> ORGANISM: Human IGF-I

<400> SEQUENCE: 4

```
Gly Pro Glu Thr Leu Cys Gly Ala Glu Leu Val Asp Ala Leu Gln
 1               5                  10                  15

Phe Val Cys Gly Asp Arg Gly Phe Tyr Phe Asn Lys Pro Thr Gly
                20                  25                  30

Tyr Gly Ser Ser Arg Arg Ala Pro Gln Thr Gly Ile Val Asp
                35                  40                  45

Glu Cys Cys Phe Arg Ser Cys Asp Leu Arg Arg Leu Glu Met Tyr
                50                  55                  60

Cys Ala Pro Leu Lys Pro Ala Lys Ser Ala
                65                  70
```

<210> SEQ ID NO 5
<211> LENGTH: 759
<212> TYPE: DNA
<213> ORGANISM: Human HSCF-II
<220> FEATURE:
<221> NAME/KEY: CDS
<222> LOCATION: 1..759

<400> SEQUENCE: 5

```
atg aag aag aca caa act tgg att ctc act tgc att tat ctt cag        45
Met Lys Lys Thr Gln Thr Trp Ile Leu Thr Cys Ile Tyr Leu Gln
 1               5                  10                  15 ctg ctc cta tct aat cct ctc gtc aaa act gaa ggg atc tgc agg        90
Leu Leu Leu Ser Asn Pro Leu Val Lys Thr Glu Gly Ile Cys Arg
                20                  25                  30 aat cgt gtg act aat aat gta aaa gac gtc act aaa ttg gtg gca       135
Asn Arg Val Thr Asn Asn Val Lys Asp Val Thr Lys Leu Val Ala
                35                  40                  45 aat ctt cca aaa gac tac atg ata acc ctc aaa tat gtc ccc ggg       180
Asn Leu Pro Lys Asp Tyr Met Ile Thr Leu Lys Tyr Val Pro Gly
                50                  55                  60 atg gat gtt ttg cca agt cat tgt tgg ata agc gag atg gta gta       225
Met Asp Val Leu Pro Ser His Cys Trp Ile Ser Glu Met Val Val
                65                  70                  75 caa ttg tca gac agc ttg act gat ctt ctg gac aag ttt tca aat       270
Gln Leu Ser Asp Ser Leu Thr Asp Leu Leu Asp Lys Phe Ser Asn
                80                  85                  90 att tct gaa ggc ttg agt aat tat tcc atc ata gac aaa ctt gtg       315
Ile Ser Glu Gly Leu Ser Asn Tyr Ser Ile Ile Asp Lys Leu Val
                95                  100                 105 aat ata gtg gat gac ctt gtg gag tgc gtg aaa gaa aac tca tct       360
Asn Ile Val Asp Asp Leu Val Glu Cys Val Lys Glu Asn Ser Ser
                110                 115                 120 aag gat cta aaa aaa tca ttc aag agc cca gaa ccc agg ctc ttt       405
Lys Asp Leu Lys Lys Ser Phe Lys Ser Pro Glu Pro Arg Leu Phe
                125                 130                 135 act cct gaa gaa ttc ttt aga att ttt aat aga tcc att aat gcc       450
Thr Pro Glu Glu Phe Phe Arg Ile Phe Asn Arg Ser Ile Asn Ala
                140                 145                 150 ttc aag gac ttt gta gtg gca tct gaa act agt gat tgt gtg gtt       495
Phe Lys Asp Phe Val Val Ala Ser Glu Thr Ser Asp Cys Val Val
                155                 160                 165 tct tca aca tta agt gga gga gga gga aag ctt gga gga gga ggc       540
Ser Ser Thr Leu Ser Gly Gly Gly Gly Lys Leu Gly Gly Gly Gly
```

-continued

```
                        170                 175                 180
tcc ggc ggc gga ccg gag acg ctc tgc ggg gct gag ctg gtg gat       585
Ser Gly Gly Gly Pro Glu Thr Leu Cys Gly Ala Glu Leu Val Asp
                185                 190                 195 gct ctt cag ttc gtg tgt gga gac agg ggc ttt tat ttc aac aag       630
Ala Leu Gln Phe Val Cys Gly Asp Arg Gly Phe Tyr Phe Asn Lys
                200                 205                 210 ccc aca ggg tat ggc tcc agc agt cgg agg gcg cct cag aca ggc       675
Pro Thr Gly Tyr Gly Ser Ser Ser Arg Arg Ala Pro Gln Thr Gly
                215                 220                 225 atc gtg gat gag tgc tgc ttc cgg agc tgt gat cta agg agg ctg       720
Ile Val Asp Glu Cys Cys Phe Arg Ser Cys Asp Leu Arg Arg Leu
                230                 235                 240 gag atg tat tgc gca ccc ctc aag cct gcc aag tca gct               759
Glu Met Tyr Cys Ala Pro Leu Lys Pro Ala Lys Ser Ala
                245                 250
```

<210> SEQ ID NO 6
<211> LENGTH: 253
<212> TYPE: PRT
<213> ORGANISM: Human HSCF-II

<400> SEQUENCE: 6

```
Met Lys Lys Thr Gln Thr Trp Ile Leu Thr Cys Ile Tyr Leu Gln
 1               5                  10                  15

Leu Leu Leu Ser Asn Pro Leu Val Lys Thr Glu Gly Ile Cys Arg
                20                  25                  30

Asn Arg Val Thr Asn Asn Val Lys Asp Val Thr Lys Leu Val Ala
                35                  40                  45

Asn Leu Pro Lys Asp Tyr Met Ile Thr Leu Lys Tyr Val Pro Gly
                50                  55                  60

Met Asp Val Leu Pro Ser His Cys Trp Ile Ser Glu Met Val Val
                65                  70                  75

Gln Leu Ser Asp Ser Leu Thr Asp Leu Leu Asp Lys Phe Ser Asn
                80                  85                  90

Ile Ser Glu Gly Leu Ser Asn Tyr Ser Ile Ile Asp Lys Leu Val
                95                  100                 105

Asn Ile Val Asp Asp Leu Val Glu Cys Val Lys Glu Asn Ser Ser
                110                 115                 120

Lys Asp Leu Lys Lys Ser Phe Lys Ser Pro Glu Pro Arg Leu Phe
                125                 130                 135

Thr Pro Glu Glu Phe Phe Arg Ile Phe Asn Arg Ser Ile Asn Ala
                140                 145                 150

Phe Lys Asp Phe Val Val Ala Ser Glu Thr Ser Asp Cys Val Val
                155                 160                 165

Ser Ser Thr Leu Ser Gly Gly Gly Gly Lys Leu Gly Gly Gly Gly
                170                 175                 180

Ser Gly Gly Gly Pro Glu Thr Leu Cys Gly Ala Glu Leu Val Asp
                185                 190                 195

Ala Leu Gln Phe Val Cys Gly Asp Arg Gly Phe Tyr Phe Asn Lys
                200                 205                 210

Pro Thr Gly Tyr Gly Ser Ser Ser Arg Arg Ala Pro Gln Thr Gly
                215                 220                 225
```

```
Ile Val Asp Glu Cys Cys Phe Arg Ser Cys Asp Leu Arg Arg Leu
                230                 235                 240

Glu Met Tyr Cys Ala Pro Leu Lys Pro Ala Lys Ser Ala
                245                 250
```